(12) United States Patent
Kim et al.

(10) Patent No.: US 10,561,854 B2
(45) Date of Patent: Feb. 18, 2020

(54) PAMS TECHNOLOGY-BASED SKIN ADHESIVE-TYPE LOW LEVEL LIGHT IRRADIATOR SYSTEM USING MOBILE COMMUNICATION DEVICE

(71) Applicant: Color Seven Co., Ltd., Seoul (KR)

(72) Inventors: Nam Gyun Kim, Seoul (KR); Kyong Jun Park, Seoul (KR); Hea Ja An, Seoul (KR)

(73) Assignee: COLOR SEVEN CO., LTD., Seoul (KR)

( * ) Notice: Subject to any disclaimer, the term of this patent is extended or adjusted under 35 U.S.C. 154(b) by 321 days.

(21) Appl. No.: 15/322,981

(22) PCT Filed: Oct. 15, 2014

(86) PCT No.: PCT/KR2014/009659
§ 371 (c)(1),
(2) Date: Dec. 29, 2016

(87) PCT Pub. No.: WO2016/060289
PCT Pub. Date: Apr. 21, 2016

(65) Prior Publication Data
US 2017/0136258 A1  May 18, 2017

(51) Int. Cl.
*A61N 5/06* (2006.01)
*H04Q 9/00* (2006.01)
(Continued)

(52) U.S. Cl.
CPC ......... *A61N 5/0616* (2013.01); *A61N 5/0622* (2013.01); *H02J 7/0021* (2013.01);
(Continued)

(58) Field of Classification Search
CPC ............... A61N 5/0616; A61N 5/0622; A61N 2005/0626; A61N 2005/0645; A61N 2005/0651; A61N 2005/0653; A61N 2005/0662; A61N 2005/067; H02J 7/0021; H02J 7/0045; H02J 7/0052; H02J 2007/0037; H02J 2007/0062;
(Continued)

(56) References Cited

U.S. PATENT DOCUMENTS

2012/0330384 A1  12/2012  Perryman et al.
2014/0206948 A1  7/2014  Romem

FOREIGN PATENT DOCUMENTS

KR       20-451945 Y1       1/2011
KR   10-2012-0065540 A      6/2012
(Continued)

*Primary Examiner* — Aaron F Roane
(74) *Attorney, Agent, or Firm* — Rabin & Berdo, P.C.

(57) ABSTRACT

The present invention relates to a photo-activated modulation of smooth muscle (PAMS) technology-based skin adhesive-type low level light irradiator system using a mobile communication device. The present invention can monitor and control the charging state of a battery embedded in a skin adhesive-type low level light irradiator, which is adhered to a specific skin area of a human body using medical double-sided tape and emits and radiates visible light for a given time period, thereby inducing a bioactive substance, such as nitric oxide, to be secreted from an internal organ or tissue of the human body which is connected to the light irradiated skin area by a peripheral nerve, in real time and wirelessly using a mobile communication device.

12 Claims, 9 Drawing Sheets

(51) Int. Cl.
 *H02J 7/00* (2006.01)
 *A61N 5/067* (2006.01)
(52) U.S. Cl.
 CPC .......... *H02J 7/0045* (2013.01); *H02J 7/0052* (2013.01); *H04Q 9/00* (2013.01); *A61N 2005/067* (2013.01); *A61N 2005/0626* (2013.01); *A61N 2005/0645* (2013.01); *A61N 2005/0651* (2013.01); *A61N 2005/0653* (2013.01); *A61N 2005/0662* (2013.01); *G08C 2201/93* (2013.01); *H02J 2007/0037* (2013.01); *H02J 2007/0062* (2013.01); *H02J 2007/0096* (2013.01); *H04Q 2209/40* (2013.01); *H04Q 2209/43* (2013.01)
(58) Field of Classification Search
 CPC .............. H02J 2007/0096; H04Q 9/00; H04Q 2209/40; H04Q 2209/43; G08C 2201/93
 USPC .......................................................... 607/89
 See application file for complete search history.

(56) References Cited

FOREIGN PATENT DOCUMENTS

| | | |
|---|---|---|
| KR | 10-1157457 B1 | 6/2012 |
| KR | 10-1181580 B1 | 9/2012 |
| KR | 10-2012-0138595 A | 12/2012 |
| KR | 10-2014-0058502 A | 5/2014 |

PAMS TECHNOLOGY-BASED SKIN ADHESIVE-TYPE LOW LEVEL LIGHT IRRADIATOR SYSTEM USING MOBILE COMMUNICATION DEVICE

TECHNICAL FIELD

The present invention relates to a low-level light irradiator system, and more particularly, to a skin adhesive-type low-level light irradiator system which is based on the photo-activated modulation of smooth muscle (PAMS) technology known as a technology for modulating smooth muscle of a human body through photoactivation and may monitor and control a charging state of a battery embedded in a skin adhesive-type low-level light irradiator and an operating state of the skin adhesive-type low-level light irradiator, which is adhered to a specific skin area of a human body using medical double-sided tape and emits and radiates visible light for a predetermined time period to induce a bioactive substance, such as nitric oxide, to be secreted from an internal organ or tissue of the human body connected to the irradiated skin area by a peripheral nerve, in real time and wirelessly using a mobile communication device.

BACKGROUND ART

In general, a low-level light therapy (LLLT) device is used to manage skin or prevent and cure various diseases by radiating the skin with visible light having an energy density of less than 2 W/cm$^2$ for a predetermined time period.

An LLLT device is known to have an effect on a tissue blood microcirculation structure or peripheral blood flow. In addition, an LLLT device is known to have effects on the promotion of cell division, cell activation, immune cells, and anti-inflammation, and on reducing pain.

According to the photo-activated modulation of smooth muscle (PAMS) technology, which is known as a new technology for modulating smooth muscle of a human body through photoactivation, a skin adhesive-type low-level light irradiator which emits visible light is adhered to a specific skin area of a human body, visible light of a specific wavelength band is radiated toward the skin area for a predetermined time period, and thus a bioactive substance, such as nitrogen monoxide, is induced to be secreted from tissue of an internal organ in the human body connected to the skin area irradiated with the visible light by a peripheral nerve. In this way, smooth muscle of an internal organ in a human body is relaxed through activation of soluble guanylate cyclase (sGC), and thus blood circulation in the internal organ is increased. Such an increase in blood circulation promotes the supply of oxygen and nutrition to damaged smooth muscle of the internal organ and boosts metabolic activity of cells, thereby curing or preventing a disease.

Among skin adhesive-type low-level light irradiators based on the PAMS technology, there are a color light acupuncturing device of Patent Literature 1 (KR20-0451945 Y1) and an adhesive color light patch of Patent Literature 2 (KR10-1181580 B1) developed by the present applicant (or inventor).

When the color light acupuncturing device is adhered to a user's neck, back, and the like or the adhesive color light patch is used under the user's clothes, the user cannot directly see the color light acupuncturing device or the color light patch. Therefore, it is not possible to determine whether the device is operating normally, and it is difficult to operate the device again.

Also, it is not possible to know a current state of a battery embedded in the color light acupuncturing device or the adhesive color light patch. Therefore, in some cases, when the color light acupuncturing device or the adhesive color light patch is adhered to a skin area using expensive medical double-sided tape and an operation switch is pressed, the device initially operates for a while and then stops due to the battery being used up, and the medical tape is wasted.

DISCLOSURE

Technical Problem

The present invention is directed to providing a photo-activated modulation of smooth muscle (PAMS) technology-based skin adhesive-type low-level light irradiator system using a mobile communication device which enables a user to wirelessly check a charging state and an available time of a battery embedded in a skin adhesive-type low-level light irradiator using the mobile communication device without seeing the low-level light irradiator in person when the skin adhesive-type low-level light irradiator, such as a color light acupuncturing device, an adhesive color light patch, and the like, is adhered to a skin area under clothes or a skin area at a position where it is difficult for the user to see the skin adhesive-type low-level light irradiator for treatment, and to wirelessly control starting and stopping of light irradiation of the skin adhesive-type low-level light irradiator in person using the mobile communication device instead of an operation switch attached to the skin adhesive-type low-level light irradiator or to check an operating state of the skin adhesive-type low-level light irradiator, an elapsed treatment time, a remaining treatment time, and the like.

Technical Solution

One aspect of the present invention provides a photo-activated modulation of smooth muscle (PAMS) technology-based skin adhesive-type low-level light irradiator system using a mobile communication device, the system including: PAMS technology-based skin adhesive-type low-level light irradiators based on a PAMS technology, which is known as a technology for modulating smooth muscle of a human body through photoactivation, and each including, in a skin adhesive-type body, a light source emitting visible light, a controller (e.g., a microcontroller unit (MCU)) controlling an intensity of the light emitted from the light source, a light irradiation pattern, and a light irradiation time period, a battery, and a wireless communicator reading and wirelessly transmitting charging state information of the battery and operating state information of the skin adhesive-type low-level light irradiators to a mobile communication device through the controller or wirelessly receiving control information for the skin adhesive-type low-level light irradiators transmitted by the mobile communication device and transferring the control information to the controller, wherein an operation switch controlling starting and stopping of light irradiation is installed on the body, an alarm unit indicating starting and stopping of light irradiation of the skin adhesive-type low-level light irradiator with sound or vibration is installed in the body, a light irradiator emitting and radiating visible light toward a skin area is formed in the body, an operation indicating light (e.g., a light-emitting diode) indicating whether the skin adhesive-type low-level light irradiator operates is installed on the body, and a charging terminal is installed on the body for charging the battery; the mobile communication device in which an application (APP) for monitoring a charging state of the battery embedded in each of the body of the skin adhesive-type low-level light irradiators and operating states of the skin adhesive-type low-level light irradiators in real time and wirelessly controlling starting and stopping of light irradiation is installed; and a charger module configured to simultaneously accommodate a plurality of skin adhesive-type low-level light irradiators for charging and storage thereof.

Advantageous Effects

The present invention can be readily used anytime and anywhere to cause a bioactive substance, such as nitric oxide, to be secreted from a specific internal organ or tissue of a human body, and can make it possible to conveniently wirelessly monitor information on a state of an embedded battery and an operating state of a skin adhesive-type low-level light irradiator in real time using a mobile communication device without attaching a display device to the skin adhesive-type low-level light irradiator. Also, it is possible to conveniently wirelessly control starting and stopping of light irradiation of the skin adhesive-type low-level light irradiator adhered to a skin area under a user's clothes or a skin area of the user's back using the mobile communication device instead of using an operation switch embedded in the skin adhesive-type low-level light irradiator in person.

MODES OF THE INVENTION

Hereinafter, exemplary embodiments of the present invention will be described in detail with reference to the accompanying drawings.

Referring to FIGS. 1 to 6, a photo-activated modulation of smooth muscle (PAMS) technology-based skin adhesive-type low-level light irradiator system 100 using a mobile communication device according to the present invention includes PAMS technology-based skin adhesive-type low-level light irradiators 100, a mobile communication device 200, and a charger module 300.

Figure 1:
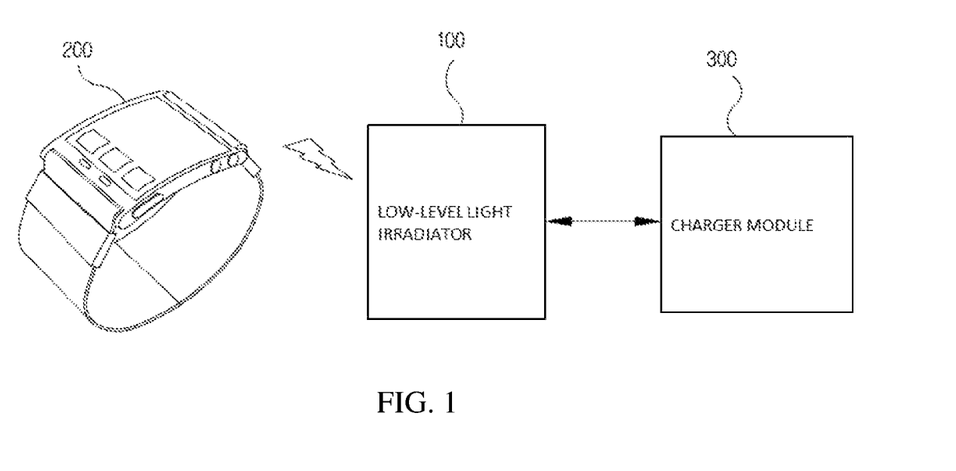
FIG. 1 shows a configuration of a photo-activated modulation of smooth muscle (PAMS) technology-based skin adhesive-type low-level light irradiator system using a mobile communication device according to an exemplary embodiment of the present invention.

The skin adhesive-type low-level light irradiators 100 are based on the PAMS technology, which is known as a technology for modulating smooth muscle of a human body through photoactivation.

Figure 3:
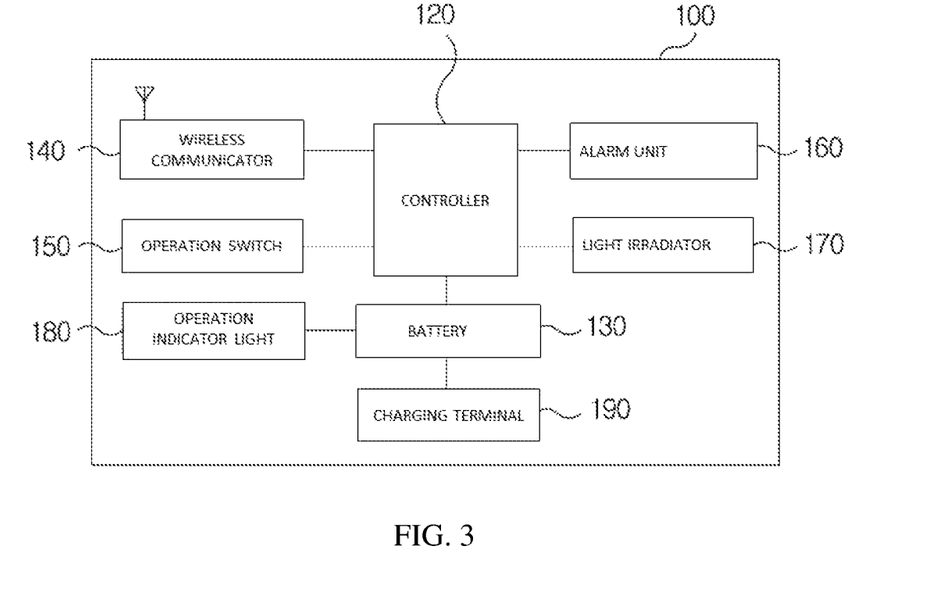
FIG. 3 is a block diagram showing a configuration of the skin adhesive-type low-level light irradiator according to the present invention.

A controller (e.g., a microcontroller unit (MCU)) 120 which controls an intensity of light emitted from a light source emitting visible light, a light irradiation pattern, and a light irradiation time period, a battery 130, and a wireless communicator 140 which reads and wirelessly transmits charging state information of the battery 130 and operating state information of the skin adhesive-type low-level light irradiator 100 to the mobile communication device 200, or wirelessly receives control information for the skin adhesive-type low-level light irradiator 100 transmitted by the mobile communication device 200 and transfers the control information to the controller 120 are embedded in a skin adhesive-type body 110 of each of the skin adhesive-type low-level light irradiators 100.

Figure 2:
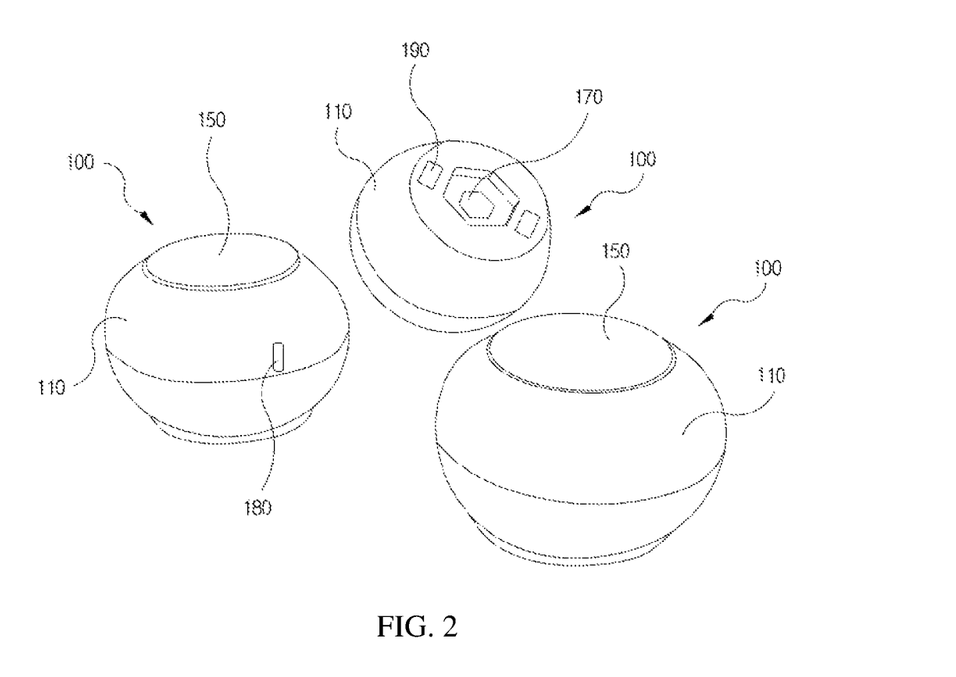
FIG. 2 shows perspective views of a skin adhesive-type low-level light irradiator according to the present invention.

The body 110 of the skin adhesive-type low-level light irradiator 100 may be manufactured with various materials, such as aluminum, titanium, duralumin, cotton, wood, rubber, polyvinyl chloride (PVC), silicon, polyurethane, etc., and is preferably manufactured in a circular, polygonal, or patch shape. For example, when the body 110 is manufactured in a circular shape, the body 110 may be manufactured in a shape identical or similar to a shape of the aforementioned color light acupuncturing device of Patent Literature 1.

The light source of the skin adhesive-type low-level light irradiator 100 preferably employs at least one of any one of a light-emitting diode (LED), an organic LED (OLED), a laser diode (LD), and a three-color LED.

The battery 130 of the skin adhesive-type low-level light irradiator 100 preferably employs a thin-film polymer battery, a coin-type battery, a paper battery, etc., and may employ a battery in a shape suitable to being embedded according to the shape of the body 110.

The wireless communicator 140 of the skin adhesive-type low-level light irradiator 100 preferably communicates with the mobile communication device 200 using radio frequency (RF) communication, Bluetooth communication, ZigBee communication, near field communication (NFC), and the like.

An operation switch 150 for controlling starting and stopping of light irradiation is installed on the body 110 of the skin adhesive-type low-level light irradiator 100.

The operation switch 150 preferably employs a press switch, a semiconductor switch in the form of an integrated circuit (IC) chip, a touch sensor, a gyro sensor, an acceleration sensor, and the like. For example, when a gyro sensor and an acceleration sensor are applied to the operation switch 150, starting and stopping of light irradiation may be controlled by a motion of a user holding and tilting the skin adhesive-type low-level light irradiator 100 or tapping or shaking the skin adhesive-type low-level light irradiator 100.

An alarm unit 160 indicating starting and stopping of light irradiation of the skin adhesive-type low-level light irradiator 100 with sound or vibration is installed in the body 110 of the skin adhesive-type low-level light irradiator 100.

A light irradiator 170 emitting and radiating visible light toward a skin area is formed in the body 110 of the skin adhesive-type low-level light irradiator 100. For example, as shown in FIG. 2, the light irradiator 170 is preferably formed as a light discharger. The light discharger may be formed in a shape identical or similar to a shape of the aforementioned color light acupuncturing device of Patent Literature 1.

An operation indicating light (e.g., an LED) 180 indicating whether the skin adhesive-type low-level light irradiator 100 is operating is installed on the body 110 of the skin adhesive-type low-level light irradiator 100.

A charging terminal 190 is installed on the body 110 of the skin adhesive-type low-level light irradiator 100 for charging the battery 130.

An application (APP) for monitoring a charging state of the battery 130 embedded in the body 110 of the skin adhesive-type low-level light irradiator 100 and an operating state of the skin adhesive-type low-level light irradiator 100 in real time and wirelessly controlling starting and stopping of light irradiation is installed in the mobile communication device 200.

The mobile communication device 200 is preferably an Android smart phone, an iPhone, an iPad, an iPod, a personal digital assistant (PDA), a wearable communication device (e.g., an iWatch, Galaxy Gear S, or the like worn on a user's wrist, a band-type communication device worn around the user's neck, arm, waist, etc., a glasses-type communication device such as Google Glasses), or the like. For example, FIG. 1 shows Galaxy Gear S.

The APP of the mobile communication device 200 preferably displays the charging state of the battery 130 embedded in the skin adhesive-type low-level light irradiator 100, a remaining available time of the battery 130, an operating state of each of the skin adhesive-type low-level light irradiators 100, starting and stopping of the skin adhesive-type low-level light irradiator 100 has been started or stopped, and a total time of use of the skin adhesive-type low-level light irradiator 100 by combining numbers, symbols, pictures, and graphs.

Figure 4:
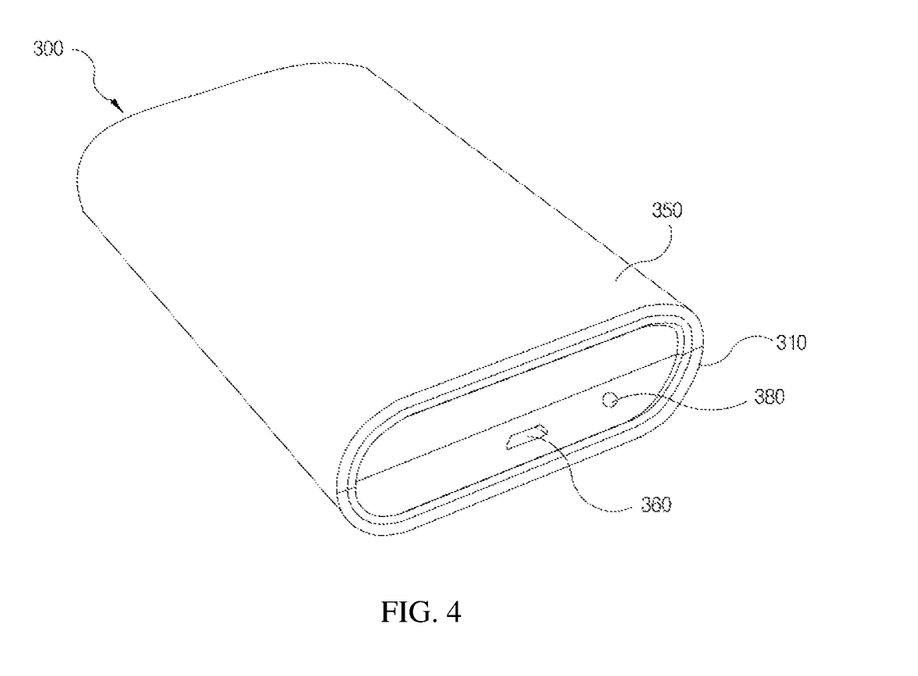
FIG. 4 is a perspective view of a charger module according to the present invention.
Figure 5:
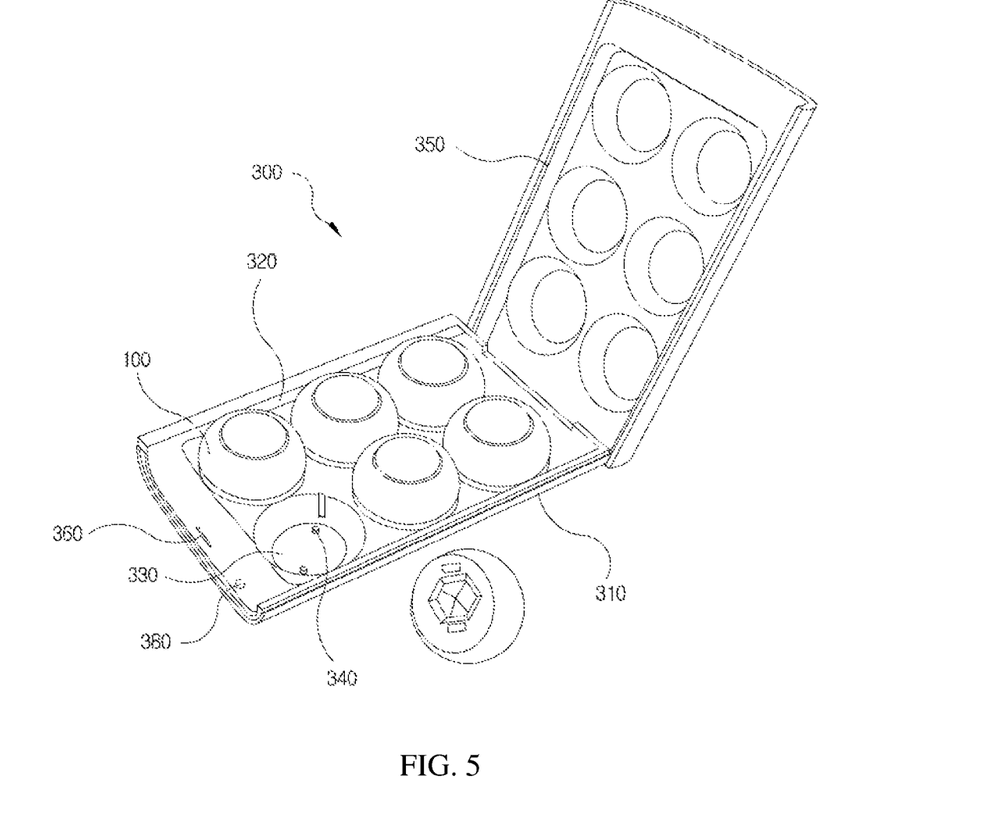
FIG. 5 is a perspective view of the charger module of FIG. 4 in which a lid thereof is open.
Figure 6:
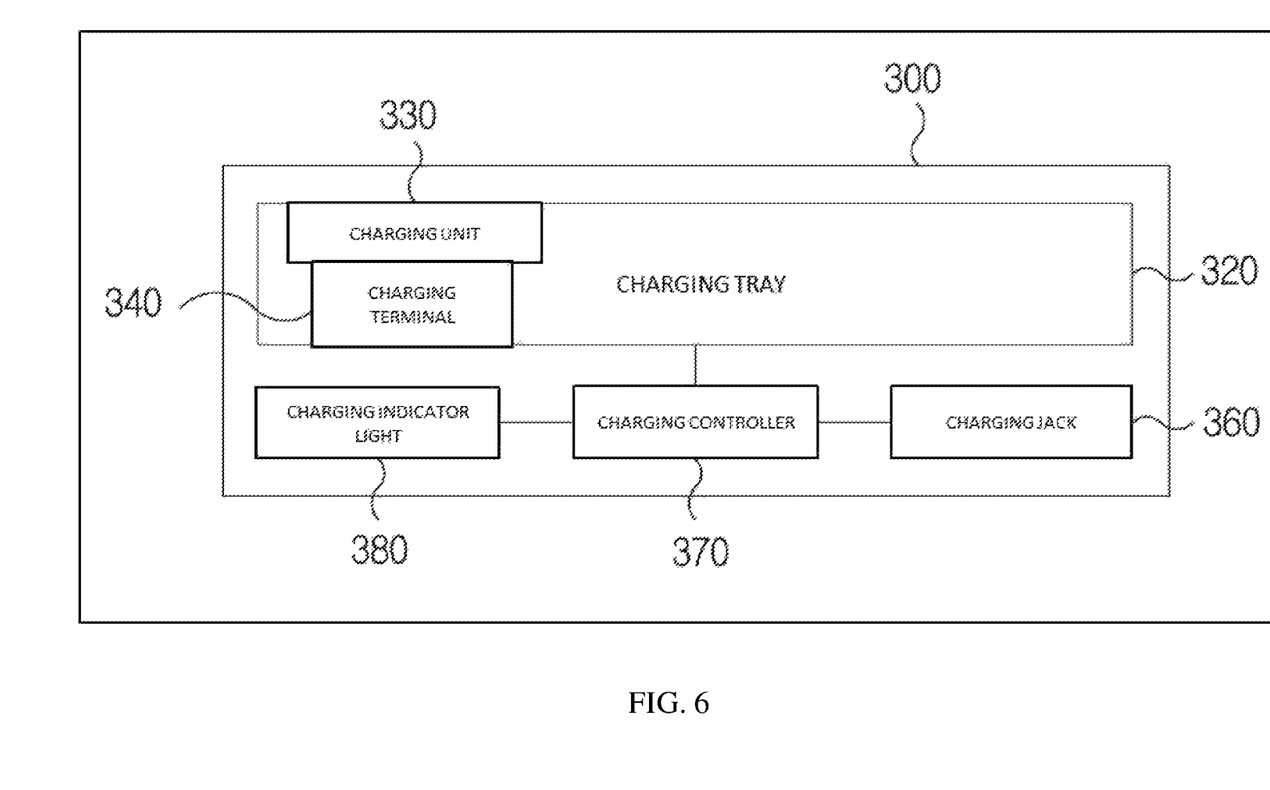
FIG. 6 is a block diagram showing a configuration of the charger module according to the present invention.

The charger module 300 may simultaneously accommodate a plurality of skin adhesive-type low-level light irradiators 100 for charging and storage thereof.

The charger module 300 has a body 310 in which a charging tray 320 is formed.

In the charging tray 320 of the charger module 300, a plurality of concave charging units 330 for accommodating the skin adhesive-type low-level light irradiators 100 are installed.

The respective charging units 330 are separated at predetermined intervals, and a charging terminal 340 electrically connected to the charging terminal 190 of the battery 130 of the skin adhesive-type low-level light irradiator 100 is installed on an upper surface of each of the charging units 330.

A lid 350 for opening or closing the body 310 of the charger module 300 is coupled to one side of the body 310 of the charger module 300 by a swingable hinge.

A charging controller 370 is supplied with power for charging the battery 130 embedded in the skin adhesive-type low-level light irradiator 100 through a charging jack 360 (e.g., a universal serial bus (USB) jack, a charging jack for a smart phone, a charging jack for an iPhone, a charging jack for an iWatch, a charging jack for Galaxy gear, etc.) formed on one side surface of the body 310 of the charger module 300, and charges the skin adhesive-type low-level light irradiators 100 accommodated in the respective concave charging units 330.

A charging indication light (e.g., an LED) 380 for indicating a charging state of the battery 130 embedded in the skin adhesive-type low-level light irradiator 100 through the charging controller 370 is further installed on one side surface of the body 310 of the charger module 300.

The charger module 300 preferably includes a charging circuit and overcharging and overheating prevention circuits therein.

The charger module 300 is preferably supplied with external power from the mobile communication device 200 connected to the charging jack 360.

The PAMS technology-based skin adhesive-type low-level light irradiator system 100 using a mobile communication device according to the present invention and configured as described above is used as follows.

FIGS. 7 to 11 show user interface (UI) screens of the mobile communication device 200 for monitoring and controlling the skin adhesive-type low-level light irradiators 100 according to an exemplary embodiment of the present invention.

The UI screens of the mobile communication device 200 shown in FIGS. 7 to 11 may be diversely modified and implemented by those of ordinary skill in the art to which the present invention pertains.

Figure 7:
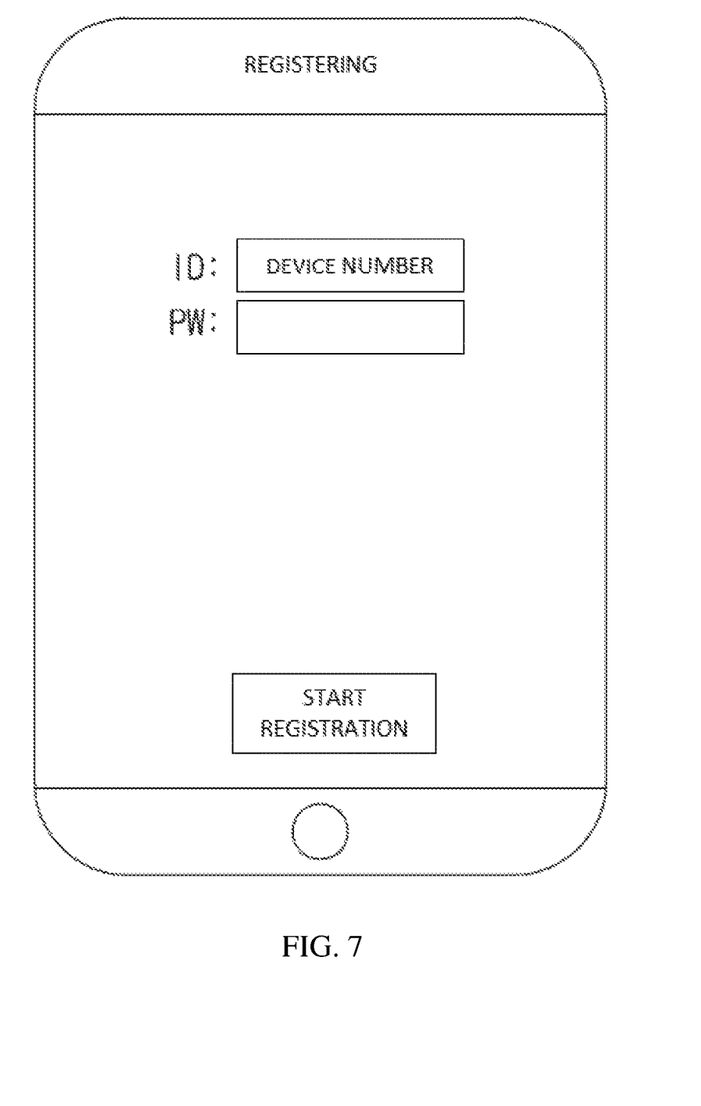
FIGS. 7 to 11 show user interface (UI) screens of a mobile communication device for monitoring and controlling skin adhesive-type low-level light irradiators according to an exemplary embodiment of the present invention.

FIG. 7 shows an embodiment of an initial screen of a case in which an APP execution icon displayed in the mobile communication device 200 for monitoring and controlling the skin adhesive-type low-level light irradiators 100 is touched. A user inputs a unique device number carved on a skin adhesive-type low-level light irradiator 100 and his or her desired password and presses a registration start button, thereby registering the skin adhesive-type low-level light irradiator 100 in the mobile communication device 200.

When the user attempts to register the plurality of skin adhesive-type low-level light irradiators 100, the user sequentially registers the skin adhesive-type low-level light irradiators 100 in the mobile communication device by repeating the registration process for each of the skin adhesive-type low-level light irradiators 100.

Figure 8:
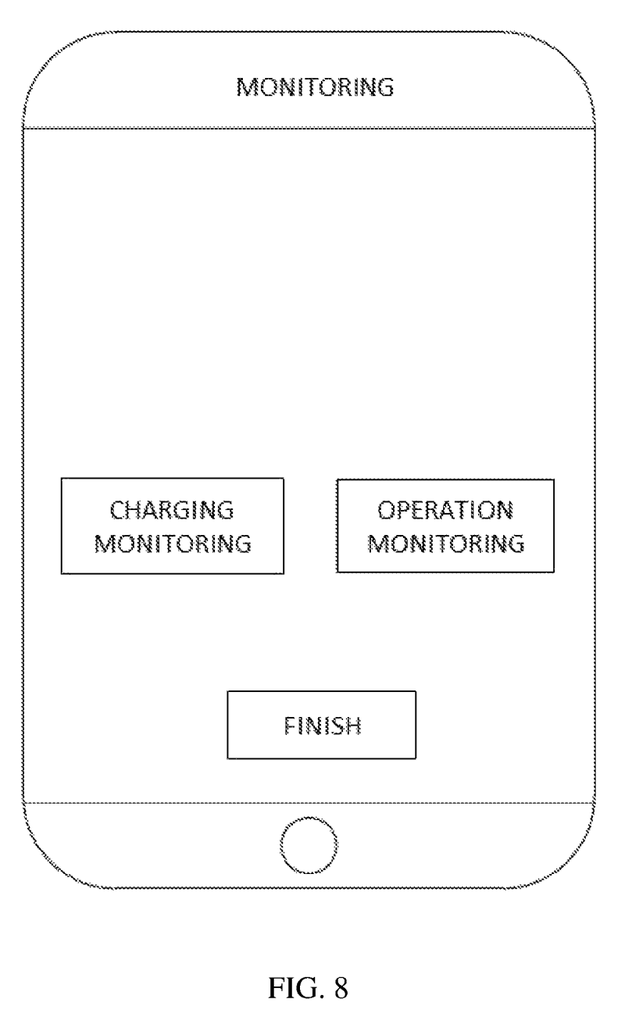

FIG. 8 shows an embodiment of a screen for selecting to just finish or to monitor the charging state of the battery 130 embedded in each of the skin adhesive-type low-level light irradiators 100 or an operating state of each of the skin adhesive-type low-level light irradiators 100.

Referring to FIG. 8, after the user registers the skin adhesive-type low-level light irradiators 100 in the mobile communication device 200, the mobile communication device 200 provides the user with a screen for selecting to just finish or to monitor the charging state of the battery 130 embedded in each of the skin adhesive-type low-level light irradiators 100 or the operating states of each of the skin adhesive-type low-level light irradiators 100.

At this time, the user monitors the charging state by pressing a monitor charging button, monitors the operating state by pressing a monitor operation button, or finishes monitoring by pressing a finish button.

Figure 9:
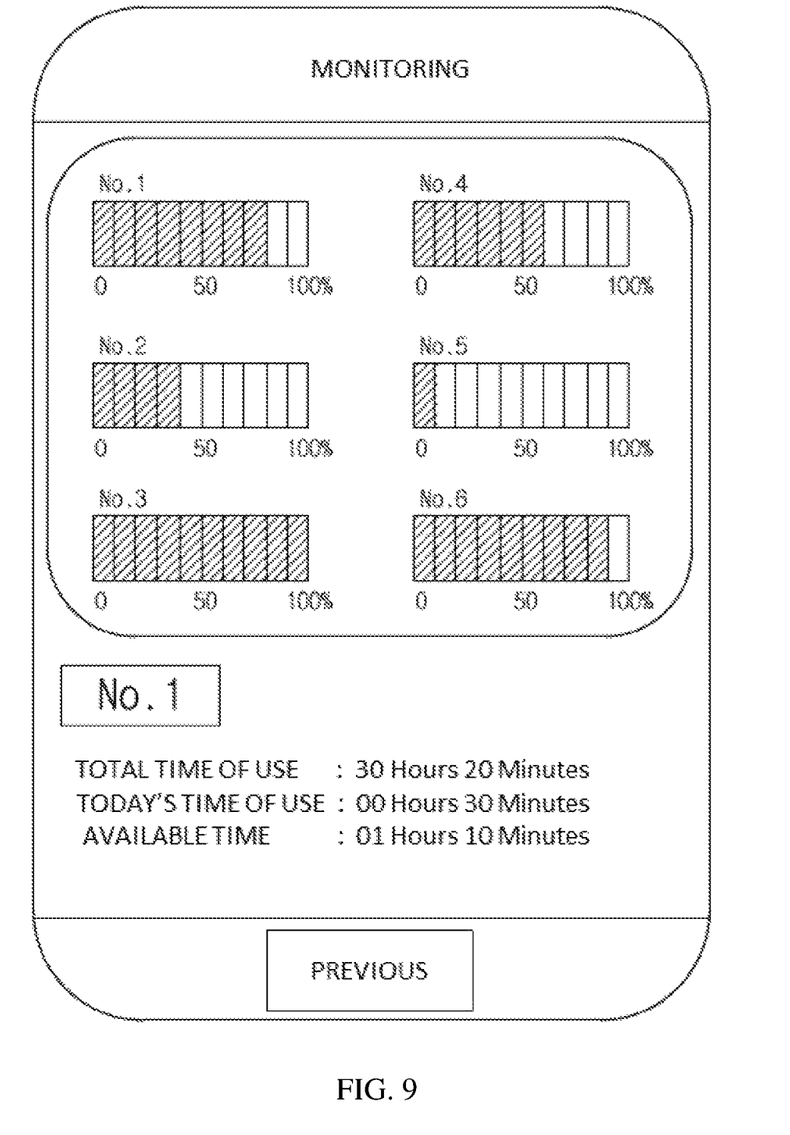

FIG. 9 shows an embodiment of a screen showing a charging state of the battery 130 embedded in each of six skin adhesive-type low-level light irradiators 100 and information, such as a total time of use and an available time of the battery 130, today's time of use of the skin adhesive-type low-level light irradiators 100, or the like, when the user selects to monitor a state of the battery 130 embedded in each of the skin adhesive-type low-level light irradiators 100 in the screen of FIG. 8.

FIG. 9 is a bar graph showing the charging state of the battery 130 of each of the six skin adhesive-type low-level light irradiators 100 (No. 1 to No. 6) in units of percentage (%).

Also, when the bar graph of the skin adhesive-type low-level light irradiator 100 (No. 1) is touched by a finger, a screen showing a total time of use, today's time of use, and an available time of the skin adhesive-type low-level light irradiator 100 (No. 1) is provided.

Figure 10:
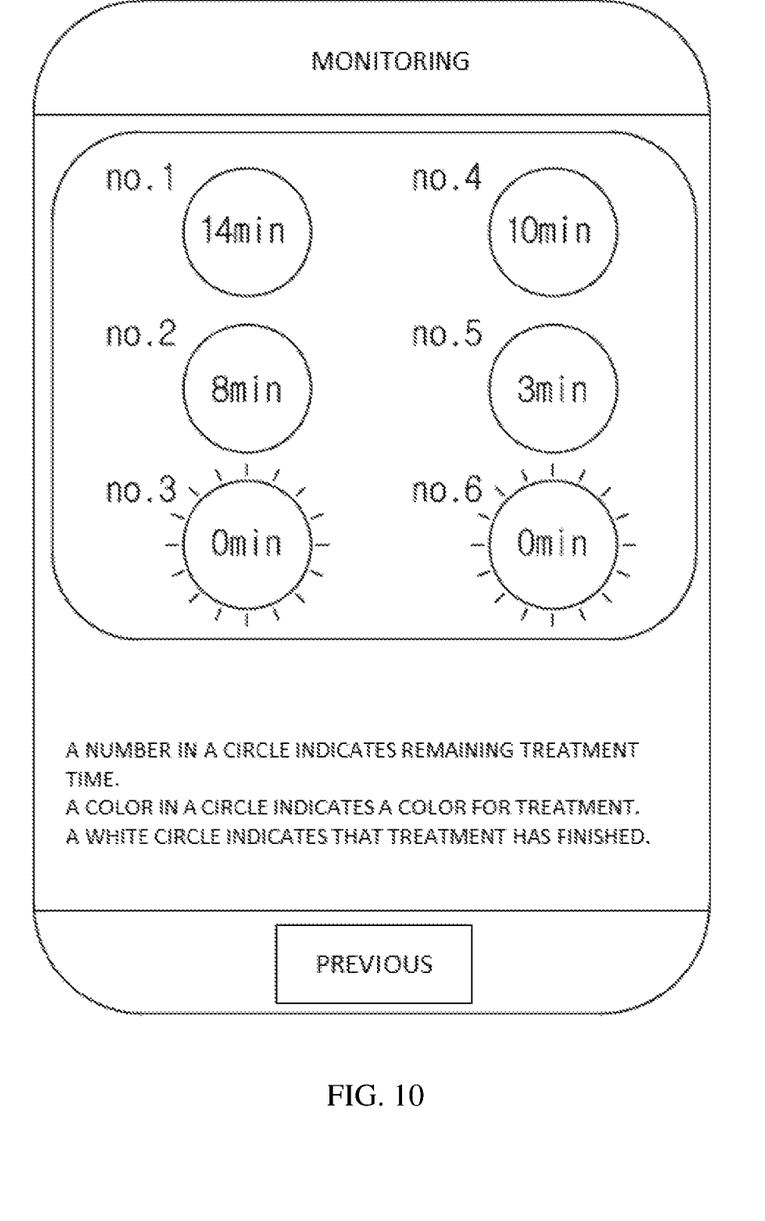

FIG. 10 shows an embodiment of a screen showing information on operating states of the six skin adhesive-type low-level light irradiators 100 to the user when the user selects to monitor the operating states of the skin adhesive-type low-level light irradiators 100 in the screen of FIG. 8.

Referring to FIG. 10, information on the operating states of the six skin adhesive-type low-level light irradiators 100 (No. 1 to No. 6) is provided through color (e.g., red, yellow, white, violet, blue, green, etc.) and time. A provided screen indicates that the skin adhesive-type low-level light irradiator 100 (No. 1) is performing treatment with blue light and 14 minutes remain therefor, the skin adhesive-type low-level light irradiator 100 (No. 2) is performing treatment with green light and 8 minutes remain therefor, the skin adhesive-type low-level light irradiator 100 (No. 3) has completed treatment with white light, the skin adhesive-type low-level light irradiator 100 (No. 4) is performing treatment with red light and 10 minutes remain therefor, the skin adhesive-type low-level light irradiator 100 (No. 5) is performing treatment with violet light and 3 minutes therefor, and the skin adhesive-type low-level light irradiator 100 (No. 6) has completed treatment.

Figure 11:
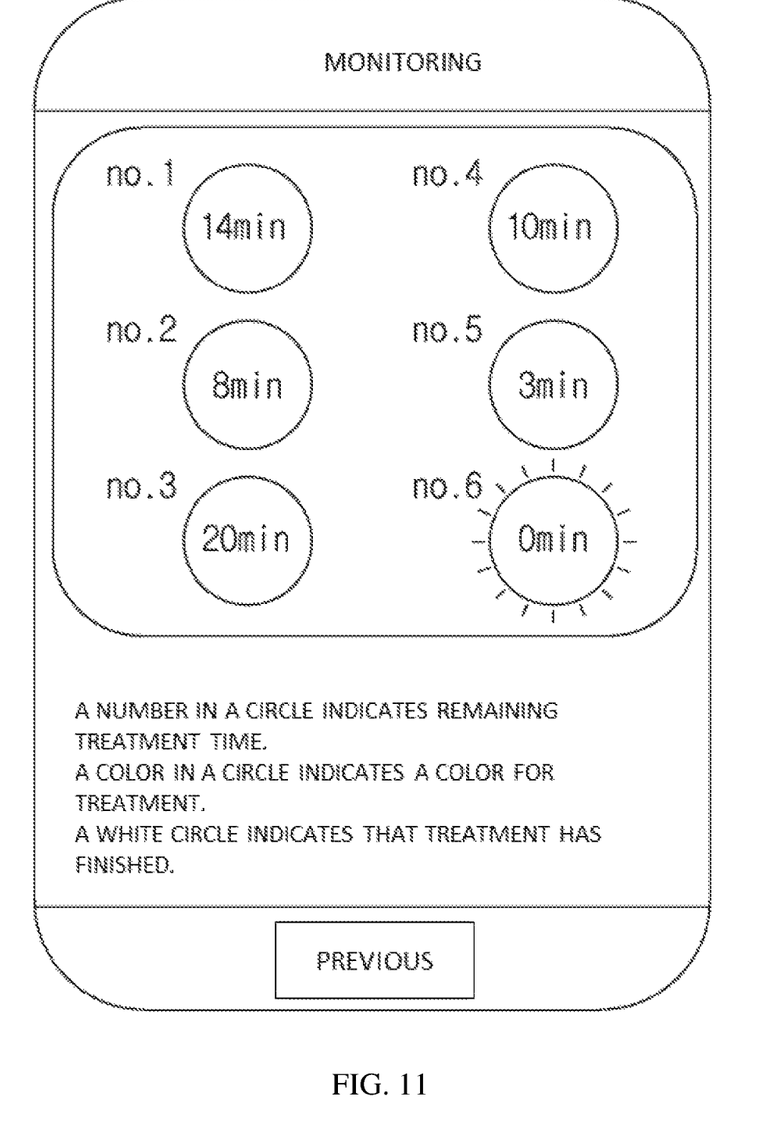

FIG. 11 provides a screen showing that the skin adhesive-type low-level light irradiator 100 (No. 3) is performing treatment with yellow light and 20 minutes remain therefor when the user touches the skin adhesive-type low-level light irradiator 100 (No. 3) having already completed treatment with his or her finger. In this way, the skin adhesive-type low-level light irradiators 100 may start or stop light irradiation while changing the light color to white, yellow, and another color each time the user touches the screen of the mobile communication device 200.

When the user presses a previous button while the screen of FIG. 10 or 11 is displayed, the screen returns to FIG. 8, and when the user presses a stop button in the screen of FIG. 8, monitoring is stopped. At this time, operation of the skin adhesive-type low-level light irradiators 100 may be automatically stopped together with the monitoring, or only the monitoring may be stopped and the operation of each of the skin adhesive-type low-level light irradiators 100 may be stopped by the user manually pressing the operation switch 150.

The above-described PAMS technology-based skin adhesive-type low-level light irradiator system according to the present invention is not limited to the exemplary embodiment, and the technical spirit thereof includes various modifications that may be made by those of ordinary skill in the art to which the present invention pertains without departing from the gist of the present invention as defined by the following claims.

What is claim is:

1. A photo-activated modulation of smooth muscle (PAMS) technology-based skin adhesive-type low-level light irradiator system using a mobile communication device, the system comprising:
   a skin adhesive-type body including skin adhesive-type low-level light irradiators;
   a controller configured to control an intensity of light emitted from a light source emitting visible light, a light irradiation pattern, and a light irradiation time period;
   a battery;
   a wireless communicator configured to read and wirelessly to transmit charging state information of the battery and operating state information of the skin adhesive-type low-level light irradiators to a mobile communication device, executed by the controller, and wirelessly to receive control information for the skin adhesive-type low-level light irradiators transmitted by the mobile communication device and to transfer the control information to the controller;
   an operation switch configured to start and stop of light irradiation;
   an alarm unit configured to indicate starting and stopping of light irradiation of the skin adhesive-type low-level light irradiator using sound or vibration;
   a light irradiator configured to emit and radiate visible light toward a skin area;
   an operation indicating light configured to indicate whether the skin adhesive-type low-level light irradiator is being installed, and a charging terminal being installed for charging the battery;
   an application being provided to the mobile communication device, the application, executed by the controller, configured to monitor a charging state of the battery embedded in the body of each of the skin adhesive-type low-level light irradiators and operating to monitor states of the skin adhesive-type low-level light irradiators in real time basis and wirelessly to control starting and stopping of light irradiation is installed; and
   a charger module configured to simultaneously accommodate a plurality of skin adhesive-type low-level light irradiators for charging and storage thereof.

2. The PAMS technology-based skin adhesive-type low-level light irradiator system of claim 1, wherein the skin adhesive-type body comprises a polygonal shape with polyvinyl chloride (PVC).

3. The PAMS technology-based skin adhesive-type low-level light irradiator system of claim 1, wherein the light source of each of the skin adhesive-type low-level light irradiators includes a light-emitting diode.

4. The PAMS technology-based skin adhesive-type low-level light irradiator system of claim 1, wherein the battery includes a coin-type battery.

5. The PAMS technology-based skin adhesive-type low-level light irradiator system of claim 1, wherein the wireless communicator uses Bluetooth communication.

6. The PAMS technology-based skin adhesive-type low-level light irradiator system of claim 1, wherein the operation switch includes a press switch.

7. The PAMS technology-based skin adhesive-type low-level light irradiator system of claim 1, wherein the mobile communication device is an iPhone.

8. The PAMS technology-based skin adhesive-type low-level light irradiator system of claim 1, wherein the application is configured to display charging state of the battery embedded in each of the skin adhesive-type low-level light irradiators, to display a remaining available time of the battery, to display an operating state of each of the skin adhesive-type low-level light irradiators, to start and stop of the skin adhesive-type low-level light irradiators, and to display a total time of use of the skin adhesive-type low-level light irradiators using at least one of numbers, symbols, pictures, and graphs.

9. The PAMS technology-based skin adhesive-type low-level light irradiator system of claim 1, wherein the charger module includes:
   a charger modular body in which a charging tray is formed;
   a plurality of concave charging units configured to accommodate the skin adhesive-type low-level light irradiators, separated at predetermined intervals, and installed in the charging tray;

a charging terminal installed on an upper surface of each of the charging units and electrically connected to the charging terminal of the battery of each of the skin adhesive-type low-level light irradiators;

a lid coupled to one side of the charger modular body of the charger module by a swingable hinge and opening or closing the charger modular body of the charger module; and a charging controller configured to control charging the battery embedded in each of the skin adhesive-type low-level light irradiators through a charging jack formed on one side surface of the charger modular body of the charger module, and charging the skin adhesive-type low-level light irradiators accommodated in the respective concave charging units.

10. The PAMS technology-based skin adhesive-type low-level light irradiator system of claim 9, wherein a charging indication light is configured to indicate charging state of the battery embedded in the skin adhesive-type low-level light irradiators through the charging controller is further installed on one side surface of the charger modular body.

11. The PAMS technology-based skin adhesive-type low-level light irradiator system of claim 9, wherein the charger module includes a charging circuit and overcharging and overheating prevention circuits therein.

12. The PAMS technology-based skin adhesive-type low-level light irradiator system of claim 9, wherein the charger module is provided with external power from the mobile communication device connected to the charging jack.

* * * * *